US008677831B2

(12) United States Patent
Chan et al.

(10) Patent No.: US 8,677,831 B2
(45) Date of Patent: Mar. 25, 2014

(54) APPARATUS AND METHOD FOR CHARACTERIZING STRESSES OF A FORMATION

(75) Inventors: Alvin Wing-Ka Chan, Houston, TX (US); Brent Alan Couzens-Schultz, Houston, TX (US)

(73) Assignee: Shell Oil Company, Houston, TX (US)

( * ) Notice: Subject to any disclaimer, the term of this patent is extended or adjusted under 35 U.S.C. 154(b) by 208 days.

(21) Appl. No.: 13/142,446

(22) PCT Filed: Dec. 29, 2009

(86) PCT No.: PCT/US2009/069626
§ 371 (c)(1),
(2), (4) Date: Aug. 16, 2011

(87) PCT Pub. No.: WO2010/078282
PCT Pub. Date: Jul. 8, 2010

(65) Prior Publication Data
US 2011/0283807 A1   Nov. 24, 2011

Related U.S. Application Data

(60) Provisional application No. 61/141,755, filed on Dec. 31, 2008.

(51) Int. Cl.
*G01N 3/24* (2006.01)
(52) U.S. Cl.
USPC .......................................... 73/845; 73/152.01

(58) Field of Classification Search
USPC .................................. 73/152.01, 152.46, 845
See application file for complete search history.

(56) References Cited

U.S. PATENT DOCUMENTS

| | | | | |
|---|---|---|---|---|
| 3,907,034 | A * | 9/1975 | Suman, Jr. | 175/50 |
| 5,282,384 | A * | 2/1994 | Holbrook | 73/152.05 |
| 5,353,637 | A * | 10/1994 | Plumb et al. | 73/152.17 |
| 5,415,030 | A | 5/1995 | Jogi et al. | 73/151 |
| 5,494,108 | A | 2/1996 | Palmer et al. | 166/308 |
| 5,540,093 | A * | 7/1996 | Levin | 73/152.01 |
| 6,351,991 | B1 * | 3/2002 | Sinha | 73/152.01 |
| 6,386,297 | B1 | 5/2002 | Cooley et al. | 175/39 |
| 6,710,861 | B2 * | 3/2004 | Fisk et al. | 356/32 |
| 7,181,380 | B2 * | 2/2007 | Dusterhoft et al. | 703/10 |
| 8,265,915 | B2 * | 9/2012 | Hsu et al. | 703/10 |
| 8,498,853 | B2 * | 7/2013 | Crawford et al. | 703/10 |
| 2007/0118292 | A1 | 5/2007 | Moos | 702/14 |

FOREIGN PATENT DOCUMENTS

WO   WO2007056278   5/2007   ............ G01R 31/08

* cited by examiner

*Primary Examiner* — Max Noori

(57) ABSTRACT

An apparatus (20) and method for characterizing stresses in a formation (10) based on leakoff pressure measured in the formation (10). The method includes determining a line of shear failure (52) as a function of leakoff pressure (LOP) measured in the formation (10), determining a vertical stress (Sv), and determining each of a lower limit ($S_{h,limit}$) and an upper limit ($S_{H,limit}$) as a function of the vertical stress ($S_v$) and the leakoff pressure (LOP).

7 Claims, 3 Drawing Sheets

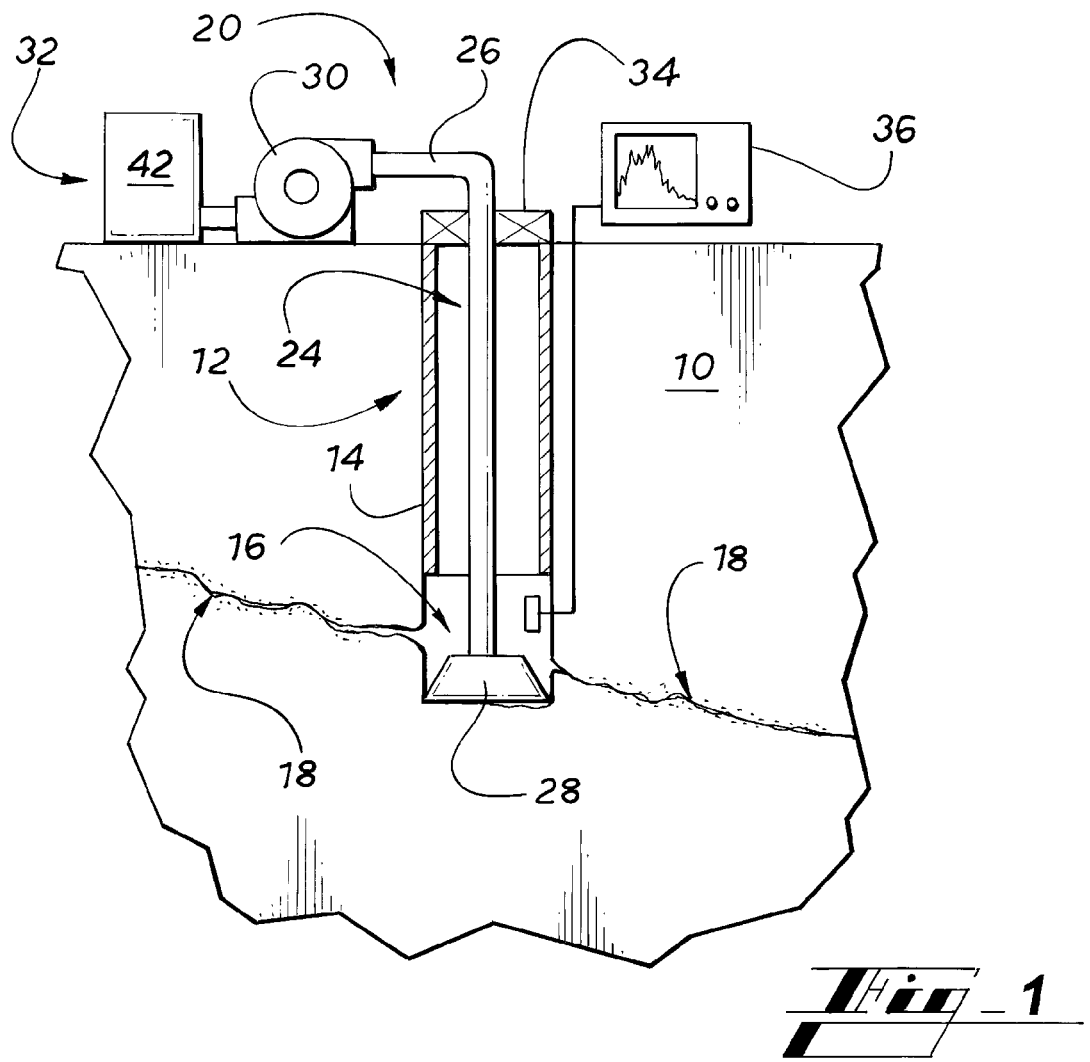
Fig_1
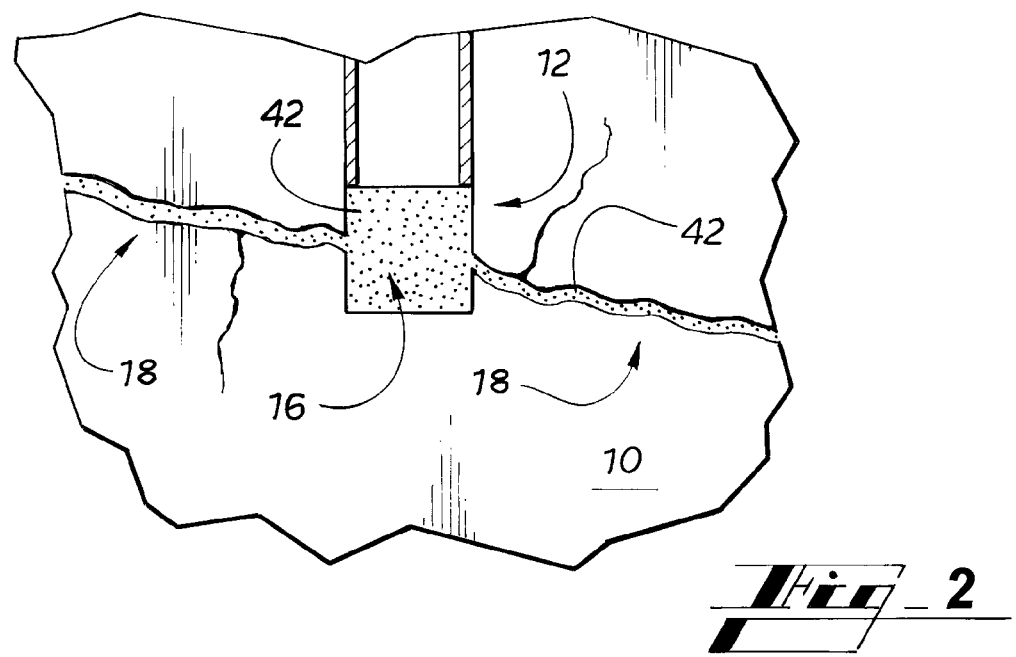
Fig_2

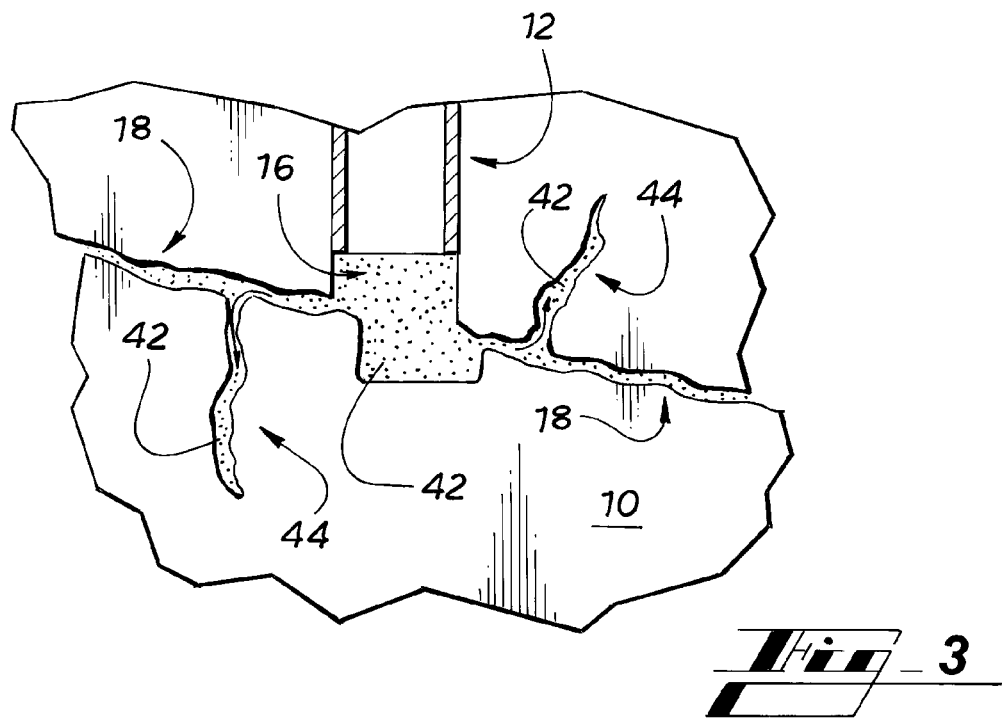
Fig_3
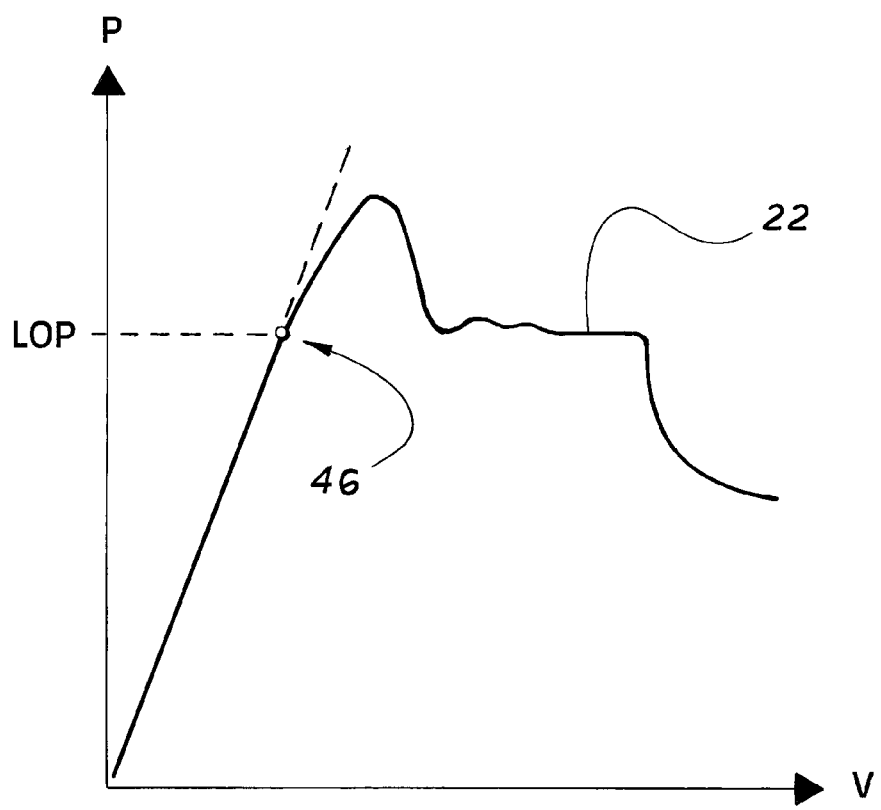
Fig_4

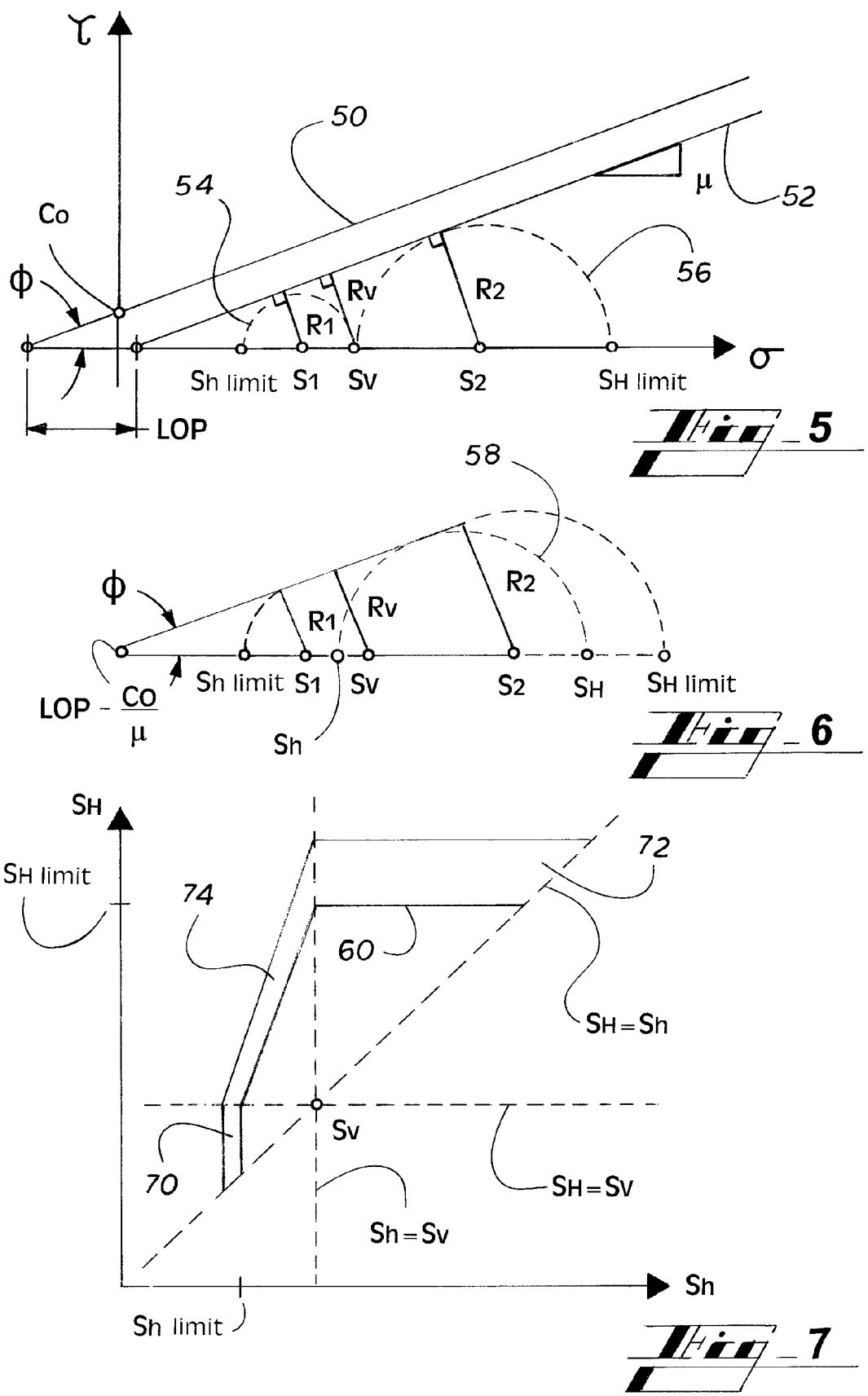

APPARATUS AND METHOD FOR CHARACTERIZING STRESSES OF A FORMATION

PRIORITY CLAIM

The present application claims priority from PCT/US2009/069626, filed 29 Dec. 2009, which claims priority from U.S. Provisional Application 61/141,755, filed 31 Dec. 2008, both of which are incorporated by reference.

TECHNICAL FIELD

This invention relates generally to apparatuses and methods for characterizing stresses of a formation.

BACKGROUND

Stress information about a formation is collected and used to make decisions associated with exploring for hydrocarbons as well as developing and producing hydrocarbons that have been discovered. For example, stress information about the formation is used in activities such as drilling margin estimation, evaluation of wellbore or borehole stability, column height estimation, determining drilling direction, determining lifespans of wells and completions, and waterflooding. If the formation is well understood, exploration, development, and production activities can be planned and executed in a cost effective and efficient manner.

The stress state and magnitudes of stresses of the formation are used in deciding how to approach exploration, development, and production activities. For example, the maximum stress magnitude is used to understand the acoustic properties of reservoirs and mudrock and to determine the porosity and volume of reservoirs. Understanding the acoustic properties of the reservoirs can facilitate increasingly accurate interpretations of acoustic measurements that are used to explore the formation. If the exploration information is accurate, there is less risk in using the information to move forward with development and production activities.

In quantifying the stress state, typically, the overburden pressure is used to determine the magnitude of the vertical stress and a leakoff test is used to determine the magnitude of the minimum stress. The leakoff test is analyzed to determine a leakoff pressure or other pressure that can be interpreted as the pressure when failure of the formation occurs during the leakoff test. The standard assumption is that the formation fails under a tensile mode of failure and the leakoff pressure represents either reopening of existing fractures or the initiation of a new tensile fracture in non-permeable rock. Leakoff pressure is generally considered to be a reasonable estimate of the minimum principle stress of the formation.

However, in certain instances, the assumption that leakoff pressure represents the minimum principle stress of the formation has been found to be inconsistent with other evidence relating to the stress state. For example, in one instance, evidence has suggested that the stress state is a reverse-fault setting or area under compression. Here, for the leakoff pressure to be considered to be reflective of the minimum stress, leakoff pressure should be near overburden pressure. In contrast, well-understood and quality controlled leakoff pressure data was observed to be well below the overburden pressure. Accordingly, leakoff pressure does not always provide a reasonable estimate of minimum principle stress that is consistent with other evidence of the stress state and the standard assumption is not applicable in every case. What is needed is a new method of characterizing formation stresses.

SUMMARY

The various embodiments of the present disclosure overcome the shortcomings of the prior art by providing an apparatus and method for characterizing stresses in a formation where the formation is under shear failure conditions. The method is applicable where a leakoff test has induced shear failure and can be used to determine stress magnitudes as a function of leakoff pressure.

According to an exemplary embodiment, a formation under shear failure conditions includes a fracture system or weak zone that intersects an openhole or uncased portion of a borehole where a leakoff test is performed. According to an exemplary method of conducting a leakoff test, the borehole is shut in and drilling fluid is pumped into the borehole to gradually increase the pressure that the formation experiences. As the pressure of the drilling fluid in the borehole is increased, the drilling fluid penetrates the fracture system, moves through permeable paths, and interacts with the stress field of the formation. As pore pressure increases in the fracture system, the formation is induced to fail along the fracture in a shear mode. The shear failure creates mixed mode fractures, opening up the nearby rock. As the rock opens up, drilling fluid moves into the openings in the rock and the pressure of the drilling fluid in the borehole decreases. The leakoff pressure can be identified as the pressure where the leakoff test pressure data substantially deviates from a gradual increase to reflect the pressure at which the formation fails.

Shear failure can be illustrated with the Mohr-Coulomb failure criterion envelope. A line of shear failure that defines the failure envelope can generally be determined with values for cohesion and a coefficient of friction. For example, values for these parameters can be determined through independent observation. Where shear failure is induced by the leakoff test, a new line of shear failure is established that is a function of the leakoff pressure. For example, the new line of shear failure can be established so as to be parallel to the initial line of shear failure and displaced from the initial line of shear failure by a function of the leakoff pressure.

A solution space that includes the possible stress states that are consistent with shear failure induced by a leakoff test can be determined. Each individual solution in the solution space consists of three mutually orthogonal stresses. According to an exemplary embodiment, the orthogonal stresses are a vertical stress, a minimum horizontal stress, and a maximum horizontal stress. The solution space itself is bound by a lower limit, which is the smallest that minimum horizontal stress can be for any possible solution, and an upper limit, which is the largest that maximum horizontal stress can be for any solution in the solution space. The limits are not the minimum and maximum horizontal stresses for one solution, but the limits for any solution in the solution space. The lower and upper limits for the horizontal stresses in the solution space are a function of the vertical stress and the line of shear failure that is a function of leakoff pressure. The vertical stress itself is a function of the overburden and is most often determined from density log data.

The lower limit and upper limit can be determined from two Mohr's circles where each Mohr's circle has the vertical stress as a principal stress and each Mohr's circle is in tangential contact with the leakoff pressure line of shear failure. The lower limit will be determined as the lower principle stress on the Mohr's circle that has the vertical stress as the maximum principle stress. The upper limit will be determined as the higher principle stress on the Mohr's circle that has the vertical stress as the minimum principle stress. Each limiting Mohr's circle is a function of overburden pressure and parameters of the line of shear failure such as cohesion and coefficient of friction.

The solution space can be broken down into three cases: a normal-fault case, a reverse-fault case, and a strike-slip fault case.

The set of stress-state solutions that represents a normal-fault setting and is consistent with shear failure includes the vertical stress and the lower limit as the principal stresses with the largest differential in magnitude. The intermediate stress, maximum horizontal stress, can vary between these two values. Here the minimum stress and intermediate stress are horizontal.

The set of stress-state solutions that represents a reverse-fault setting and is consistent with shear failure includes the vertical stress and the upper limit as the principal stresses with the largest differential in magnitude. The intermediate stress, minimum horizontal stress, can vary between these two values. Here, the maximum stress and intermediate stress are horizontal.

The set of stress-state solutions that represents a strike-slip fault setting and is consistent with shear failure includes the minimum horizontal stress and the maximum horizontal stress as the principal stresses with the largest differential in magnitude. The minimum horizontal stress value may not exceed lower limit and the maximum horizontal stress value may not exceed the upper limit. The minimum horizontal stress and the maximum horizontal stress values are determined as pairs from a series of Mohr's circles that are in tangential contact with the line of shear failure that is a function of leakoff pressure. The intermediate stress in this case is vertical stress. Here the maximum stress and minimum stress are horizontal.

The foregoing has broadly outlined some of the aspects and features of the present invention, which should be construed to be merely illustrative of various potential applications of the invention. Other beneficial results can be obtained by applying the disclosed information in a different manner or by combining various aspects of the disclosed embodiments. Accordingly, other aspects and a more comprehensive understanding of the invention may be obtained by referring to the detailed description of the exemplary embodiments taken in conjunction with the accompanying drawings, in addition to the scope of the invention defined by the claims.

BRIEF DESCRIPTION OF THE DRAWINGS

FIG. 1 is a partial view a formation and an apparatus for conducting a leakoff test in an openhole portion of a borehole in the formation, according to an exemplary embodiment of the disclosure.

FIGS. 2 and 3 are partial views of the formation of FIG. 1, illustrating leakoff test induced shear failure of the formation.

FIG. 4 is a graphical illustration of leakoff test data.

FIG. 5 is a graphical illustration of Mohr-Coulomb shear failure criteria that represents leakoff test induced shear failure of the formation.

FIG. 6 is a graphical illustration corresponding to FIG. 5 of a geometrical relationship between potential horizontal principle stresses.

FIG. 7 is a graphical illustration of a stress polygon that represents the potential horizontal principle stresses of the formation.

DETAILED DESCRIPTION

As required, detailed embodiments are disclosed herein. It must be understood that the disclosed embodiments are merely exemplary and other embodiments may be embodied in various and alternative forms, and combinations thereof, without departing from the scope of the teachings of the disclosure. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods have not been described in detail in order to avoid obscuring the disclosure. Therefore, specific structural and functional details disclosed herein are not to be interpreted as limiting, but merely as a basis for the claims and as a representative basis for teaching one skilled in the art.

Formation and Apparatus

Referring to FIG. 1, an exemplary formation 10 is illustrated. A borehole 12 is drilled in formation 10 and a casing string 14 is cemented along a portion of borehole 12. As used herein, the term "formation" generally refers to the rock around the borehole or otherwise to a body of rock. An openhole 16 or uncased portion of borehole 12 is intersected by a permeable fracture system 18 or weak zone in formation 10.

As used herein, the term "in situ" refers to the original location or position, such as a formation that has not been disturbed by faults or landslides.

An exemplary apparatus 20 for drilling borehole 12 and for collecting leakoff test data 22 (FIG. 4) includes a drillstring 24, a drillpipe 26, a drill bit 28, a drilling fluid pump 30, a drilling fluid reservoir 32, a borehole seal 34, and a data acquisition unit 36. During the drilling operations, apparatus 20 is used to shut in borehole 12 and gradually increase the pressure that formation 10 at the bottom of borehole 12 experiences. At a certain pressure, fluids will enter formation 10, i.e., fluids will leakoff. The results of the procedure dictate the maximum pressure that may be applied to that portion of borehole 12 during drilling operations. This procedure is accomplished by pumping drilling fluid 42 into the borehole 12. Drilling fluid 42, also known as drilling mud, refers to any number of liquid fluids and mixtures of fluids and solids used in operations to drill boreholes into the earth.

Shear Failure Conditions

Formation 10 is under shear failure conditions along the permeable fracture system 18 such that, as a leakoff test is conducted, formation 10 fails in a shear failure mode. Different stress states can lead to shear failure so long as the differential between principle stresses is sufficiently high. A stress state can be represented by three principle stresses that are orthogonal to one another. In the exemplary embodiment, the three principle stresses include a minimum horizontal stress $S_h$, a maximum horizontal stress $S_H$, and a vertical stress $S_v$. For purposes of teaching, the minimum horizontal stress $S_h$ is smaller than the maximum horizontal stress $S_H$.

For purposes of illustration, the illustrated formation is considered to be in compression with horizontal stresses $S_h$, $S_H$ being greater than the vertical principle stress $S_v$.

Overburden pressure can be used to determine a value of the vertical principle stress $S_v$. Overburden pressure, also known as lithostatic pressure or geostatic pressure, is the pressure or stress imposed on a layer of soil or rock by the weight of the overlying material. A value for overburden pressure at a depth can be determined as a function of the density of the overlying rock.

Leakoff Test (LOT) and Shear Failure

Before borehole 12 is drilled to a next casing depth, a leakoff test is performed at openhole 16 to determine the maximum pressure or mudweight that can be applied when drilling to the next casing depth without failing at the current casing shoe (not shown). Casing shoe is the bottom of casing string 14 including the cement around it. It serves to isolate formation 10 from drilling fluids 42 in the casing string 14 and in openhole 16 of borehole 12.

An exemplary method of performing a leakoff test is now described. Referring to FIG. 1, borehole 12 is closed with seal 34 and drilling fluid 42 is pumped into openhole 16 of borehole 12 through drill pipe 26. Referring to FIGS. 1 and 4, the fluid pressure in borehole 12 gradually increases until formation 10 fails at openhole 16. In general, formation 10 can fail in a shear mode or in a tensile mode. To illustrating a new interpretation of stress state where shear failure conditions are assumed or known (in contrast to assuming tensile failure conditions), a shear failure mode of formation 10 is described in further detail.

Referring to FIGS. 2-4, as the pressure of drilling fluid 42 in openhole 16 is increased, drilling fluid 42 penetrates and interacts with fracture system 18. The pressure of drilling fluid 42 in fracture system 18 works against cohesion $C_0$ and friction $\mu$ in fracture system 18 until formation 10 is induced to fail in a shear mode. The failure of formation 10 creates volumes 44 into which drilling fluid 42 can move from openhole 16. Volumes 44 can be new fractures, pores that are opened, or opening of fractures with increased displacement between the walls of fracture system 18 due to asperities along the walls of fracture system 18. As drilling fluid 42 moves from openhole 16 into volumes 44, the pressure of drilling fluid 42 in borehole 12 drops.

The leakoff test measures the pressure in borehole 12 with respect to the volume of drilling fluid 42 that is pumped into borehole 12 or with respect to time. Factors that contribute to variations in leakoff data results include different pump rates, the use of hesitation testing, and the type of drilling fluid.

Leakoff Pressure (LOP)

Failure of the formation can be observed in the leakoff test data 22. For example, referring to FIG. 4, the leakoff test data 22 include a data point 46, reflective of a value of leakoff pressure LOP, where the leakoff test data 22 begins to deviate from a linear increase in pressure. Generally, the linear increase in pressure is due to pumping drilling fluid 42 into borehole 12 as the volume of borehole 12 and fracture system 18 is substantially fixed. The pressure in borehole 12 gradually builds until formation 10 fails and the volume of borehole 12 and fracture system 18 is essentially increased as volumes 44 open up. By identifying leakoff pressure LOP where the deviation occurs, leakoff pressure LOP reflects the pressure at failure. It should be noted that leakoff pressure can be alternatively identified and other parameters that reflect the failure of the formation can be substituted for leakoff pressure.

The leakoff test data 22 can be used to determine the maximum pressure limit for drilling an additional casing length, to determine casing placement for the borehole being drilled, to determine stress information in formation 10 for borehole stability analyses in future boreholes, for development issues, and for exploration of issues such as trap integrity and column height predictions in other prospects.

Method of Using Leakoff Pressure to Characterize Stress of Formation

Referring to FIG. 5, Mohr-Coulomb failure criterion can be used to quantify the magnitude of stresses of formation 10 based on leakoff pressure LOP. In situ or far field stresses are considered to control shear failure along fracture system 18. Further, the pressure of drilling fluid 42 in fracture system 18 is considered to be substantially the same as the pressure of drilling fluid 42 in borehole 12.

The Mohr-Coulomb criterion is illustrated on a graph where normal stresses are plotted along the x-axis and shear stresses are plotted along the y-axis. A notional line of shear failure 50 that defines a failure envelope is plotted on the graph. Line of shear failure 50 can be determined by selecting values for cohesion $C_0$ and angle of friction $\mu$ and is given by $\tau_f = \mu \cdot \sigma_f + C_0$ where $\tau_f$ is shear stress at failure and $\sigma_f$ is tensile stress at failure. However, notional line of shear failure 50 does not take leakoff pressure LOP into account.

Since the leakoff test induces shear failure, a leakoff pressure line of shear failure 52 that takes leakoff pressure LOP into account is established and represents that shear failure is a function of leakoff pressure LOP. Leakoff pressure line of shear failure 52 is parallel to notional line of shear failure 50 and is displaced from notional line of shear failure 50 along the x-axis by the magnitude of leakoff pressure LOP. Leakoff pressure line of shear failure 52 is given by $\tau_f = \mu \cdot (\sigma_f - LOP) + C_0$.

Leakoff pressure line of shear failure 52 can be considered to represent the failure envelope where in situ stresses on formation 10 cause shear failure on the fracture or permeable system 18 during the leakoff test. Given the vertical stress $S_v$ according to the overburden pressure and the leakoff pressure line of shear failure 52, Mohr's circles 54, 56 can be constructed to determine a lower limit $S_{h,limit}$ and an upper limit $S_{H,limit}$ that are consistent with shear failure on the permeable fracture system 18.

Vertical stress $S_v$ is determined at a depth where the leakoff test is performed and plotted as a point on the x-axis. Mohr's circles 54, 56 are constructed such that each one has vertical stress $S_v$ as a principle stress and each is in tangential contact with leakoff pressure line of shear failure 52.

The two Mohr's circles 54, 56 represent solutions in the normal-fault and reverse-fault stress states respectively. The other principle stress determined by Mohr's circle 54 is the lower limit $S_{h,limit}$, which is the smallest that the minimum horizontal stress $S_h$ can be for any possible solution in the solution space. The lower limit $S_{h,limit}$ corresponds to the normal-fault stress state solutions. The other principle stress determined by Mohr's circle 56 is the upper limit $S_{H,limit}$, which is the largest that the maximum horizontal stress $S_H$ can be for any possible solution in the solution space. The upper limit $S_{H,limit}$ corresponds to the reverse-stress state solutions. Any number of Mohr's circles, such as Mohr's circle 58, can be drawn in tangential contact with the leakoff pressure line of shear failure 52 where the principle stresses are between the lower limit $S_{h,limit}$ and the upper limit $S_{H,limit}$ in magnitude. Such Mohr's circles correspond to strike-slip stress state solutions where vertical stress $S_v$ is the intermediate stress.

Lower limit $S_{h,limit}$ and upper limit $S_{H,limit}$ can be determined as a function of vertical stress $S_v$, leakoff pressure LOP, cohesion $C_0$, and coefficient of friction p. Exemplary equations for determining lower limit $S_{h,limit}$ and upper limit $S_{H,limit}$ are now described. Referring to FIGS. 5 and 6, since the leakoff pressure line of shear failure 52 is tangent to each of Mohr's circles 54, 56, a radial line $R_1$, $R_2$ extends from the center point $S_1$, $S_2$ of each of Mohr's circles 54, 56 to perpendicularly intersect the leakoff pressure line of shear failure 52. Similarly, a radial line $R_v$ extends from the point of vertical stress $S_v$ to perpendicularly intersect leakoff pressure line of shear failure 52. The radial lines $R_1$, $R_2$, $R_v$ are parallel to one another and the lengths of the radial lines $R_1$, $R_2$, $R_v$ are geometrically related to one another. The geometrical relationships can be given as $$\frac{R_1}{S_1 - (LOP - C_0/\mu)} = \frac{R_v}{S_v - (LOP - C_0/\mu)} = \frac{R_2}{S_2 - (LOP - C_0/\mu)}.$$

The radii $R_1$, $R_2$ relate the center points $S_1$, $S_2$ to the vertical stress $S_v$ according to $S_1=S_v-R_1$ and $S_2=S_v+R_2$ and relate the lower and upper limits $S_{h,limit}$, $S_{H,limit}$ to the vertical stress $S_v$ according to $S_{h,min}=S_v-2R_1$ and $S_{H,max}=S_v+2R_2$. Also, an angle $\phi$ is given as $\phi=\tan^{-1}(\mu)$ and the radial line $R_v$ is given by $R_v=(S_v-(LOP-C_0/\mu))\sin\phi$.

These relationships can be used to determine the lower and upper limits $S_{h,limit}$, $S_{H,limit}$. For example, the lower and upper limits $S_{h,limit}$, $S_{H,limit}$ can be given as $$S_{h,limit} = S_v - \frac{2(S_v - (LOP - C_0/\mu))\sin\phi}{(1+\sin\phi)}$$

and $$S_{H,limit} = S_v + \frac{2(S_v - (LOP - C_0/\mu))\sin\phi}{(1-\sin\phi)}.$$

The magnitudes of the lower and upper limits $S_{h,limit}$, $S_{H,limit}$ can then be determined.

A stress state solution space that includes stress states that are consistent with shear failure induced by a leakoff test can be determined. Each stress state solution of the exemplary stress state solution space includes three mutually orthogonal stresses: the vertical stress $S_v$, the minimum horizontal stress $S_h$, and the maximum horizontal stress $S_H$. The solution space itself is bound by the lower limit $S_{h,limit}$, which is the smallest the minimum horizontal stress $S_h$ can be, and the upper limit $S_{H,limit}$, which is the largest the maximum horizontal stress $S_H$ can be for any solution in the solution space. As described above, the limits $S_{h,limit}$, $S_{H,limit}$ are a function of the vertical stress $S_v$ and the leakoff pressure LOP.

The solution space can be broken down into three cases: a normal-fault case where $S_v \geq S_H \geq S_h$, a reverse-fault case where $S_H \geq S_h \geq S_v$, and a strike-slip fault case where $S_H \geq S_v \geq S_h$.

The set of stress state solutions that represents a normal-fault setting and is consistent with shear failure includes vertical stress $S_v$ and lower limit $S_{h,limit}$ as the principal stresses with the largest differential in magnitude. The intermediate stress, maximum horizontal stress $S_H$, can vary between these two values. Here the minimum stress and intermediate stress are horizontal.

The set of stress state solutions that represents a reverse-fault setting and is consistent with shear failure includes vertical stress $S_v$ and upper limit $S_{H,limit}$ as the principal stresses with the largest differential in magnitude. The intermediate stress, minimum horizontal stress $S_h$, can vary between these two values. Here the maximum stress and intermediate stress are horizontal.

The set of stress state solutions that represents a strike-slip fault setting and is consistent with shear failure includes minimum horizontal stress $S_h$ and maximum horizontal stress $S_H$ as the principal stresses with the largest differential in magnitude where $S_h < S_v$ and $S_H > S_v$. These values may not exceed or fall outside of lower limit $S_{h,limit}$ or upper limit $S_{H,limit}$ and they are determined as pairs from a series of Mohr's circles that are in tangential contact with the leakoff pressure line of shear failure 52. The intermediate stress in this case is vertical stress $S_v$. Here the maximum stress and minimum stress are horizontal.

Stress Polygon

Referring to FIG. 7, once values of lower and upper limits $S_{h,limit}$, $S_{H,limit}$ have been determined, a stress polygon can be used to illustrate the potential range of the horizontal stresses $S_h$, $S_H$ and the possible stress regimes. Minimum horizontal stress $S_h$ is plotted along the x-axis and maximum horizontal stress $S_H$ is plotted along the y-axis.

The stress polygon line produced by the method described herein allows stress magnitude estimation for all three stress regimes. For purposes of illustration, a stress polygon line 60 is plotted. Stress polygon line 60 includes a vertical segment that represents the set of stress states solutions corresponding to a normal-fault setting 70, a horizontal segment that represents the set of stress state solutions corresponding to a reverse-fault setting 72, and a diagonal segment that represents the set of stress state solutions corresponding to a strike-slip fault setting 74. The diagonal segment connects the vertical segment and the horizontal segment.

Where cohesion $C_0$ and/or coefficient of friction $\mu$ include a range of possible values, stress polygon lines can define an area of the stress polygon where possible stress magnitudes are located. For example, a stress polygon line corresponding to a first coefficient of friction and a stress polygon line corresponding to a second coefficient of friction can define a stress polygon area there between.

It should be noted that the shear failure method of determining stress is not necessarily intended to replace the prior assumption of tensile failure during a leakoff test. Rather, it can be regarded as an alternative interpretation. Determining when to use the shear failure assumption is dependent on the interpreter's understanding of the subsurface geology. It is appropriate to consider using the shear failure method of determining stress when leakoff tests are lower than expected as well as other explanations for a lower than expected leakoff which include but are not limited to stopping the test before failure, poor shoe integrity, poor control on volumes and rates, and the like.

The disclosure has been illustrated in relation to particular embodiments, which are intended in all respects to be illustrative rather than restrictive. Those skilled in the art will recognize that the disclosure is capable of many modifications and variations without departing from the scope of the disclosure.

The above-described embodiments are merely exemplary illustrations of implementations set forth for a clear understanding of the principles of the disclosure. Variations, modifications, and combinations may be made to the above-described embodiments without departing from the scope of the claims. All such variations, modifications, and combinations are included herein by the scope of this disclosure and the following claims. For example, we have discussed the method mainly in the context of compressive, reverse-fault stress settings, but it may be applied to normal-fault and strike-slip stress settings. Similarly, we have discussed the method in terms of leakoff tests, but it may also be applied to other operations or drilling events that provide information on stress conditions, such as, but not limited to, lost circulation events or production tests.

The invention claimed is:

1. A method for determining a stress state solution space for a formation, comprising:
    a) determining a line of shear failure as a function of leakoff pressure measured in the formation;
    b) determining a vertical stress; and
    c) determining each of a lower limit and an upper limit as a function of the vertical stress and the leakoff pressure, wherein the lower limit is the smallest that the minimum horizontal stress can be for any possible solution and the upper limit is the largest that the maximum horizontal stress can be for any solution in the solution space, and wherein each of the lower limit and the upper limit is a principle stress of a respective Mohr's circle that is in tangential contact with the line of shear failure, the vertical stress being the other principle stress of the Mohr's circles;

wherein the stress state solution space comprises stress state solutions for each of normal-fault, reverse-fault, and strike-slip conditions.

2. The method of claim 1, further comprising generating an output representing the stress state solution space.

3. The method of claim 2, herein the output consists entirely or in part of a stress polygon, a visual representation, or machine readable instructions.

4. The method of claim 2, the output comprising a stress polygon representing the stress state solution space in reverse-fault, normal-fault, and strike-slip conditions.

5. A method for determining a stress state solution space for a formation, comprising:

a) determining a line of shear failure as a function of leakoff pressure measured in the formation, the line of shear failure being a function of one of: cohesion and the coefficient of friction;

b) determining a vertical stress; and c) determining each of a lower limit and an upper limit as a function of the vertical stress and the leakoff pressure, wherein the lower limit is the smallest that the minimum horizontal stress can be for any possible solution and the upper limit is the largest that the maximum horizontal stress can be for any solution in the solution space, and wherein each of the lower limit and the upper limit is a principle stress of a respective Mohr's circle that is in tangential contact with the line of shear failure, the vertical stress being the other principle stress of the Mohr's circles.

6. The method of claim 5, further comprising determining one principle stresses of the Mohr's circle as a function of overburden pressure.

7. The method of claim 1, further comprising determining one principle stresses of the Mohr's circle as a function of overburden pressure.

* * * * *